United States Patent [19]

Murofushi et al.

[11] Patent Number: 5,493,015

[45] Date of Patent: Feb. 20, 1996

[54] METHOD FOR REDUCING CONTAMINATIVE LIVE BACTERIA IN XANTHAN GUM

[75] Inventors: Kanji Murofushi, Joetsu; Shigehiro Nagura, Niigata, both of Japan

[73] Assignees: Shin-Etsu Chemical Co. Ltd., Tokyo, Japan; Shin-Etsu Bio, Inc., San Diego, Calif.

[21] Appl. No.: 226,266

[22] Filed: Apr. 11, 1994

[51] Int. Cl.$^6$ ............................ C07H 1/06; C07H 1/08; C08B 37/00

[52] U.S. Cl. ............................ 536/127; 536/114

[58] Field of Search .................... 536/127, 114

[56] References Cited

U.S. PATENT DOCUMENTS

| | | | |
|---|---|---|---|
| 3,206,275 | 9/1965 | Sair et al. | 536/127 |
| 3,516,983 | 6/1970 | Colegrove | 536/114 |
| 3,919,189 | 11/1975 | Empey et al. | 536/127 |
| 4,051,317 | 9/1977 | Towle | 536/114 |
| 4,053,699 | 10/1977 | Cahalan et al. | 536/114 |
| 4,070,535 | 1/1978 | Empey et al. | 536/114 |
| 4,135,979 | 1/1979 | Corley et al. | 536/114 |
| 4,259,477 | 3/1981 | Kang | 536/114 |
| 4,269,974 | 5/1981 | Wintersdorff | 536/114 |
| 4,667,026 | 5/1987 | Jarry et al. | 536/114 |
| 4,978,750 | 12/1990 | Wilke et al. | 536/114 |
| 4,983,731 | 1/1991 | Wagner et al. | 536/127 |
| 5,198,469 | 3/1993 | Sakata | 536/114 |
| 5,315,003 | 5/1994 | Maruyama et al. | 536/127 |

FOREIGN PATENT DOCUMENTS

| | | |
|---|---|---|
| 0028446 | 5/1981 | European Pat. Off. . |
| 0068706 | 1/1983 | European Pat. Off. . |
| 0338307 | 10/1989 | European Pat. Off. . |
| 2606423 | 5/1988 | France . |
| 17575 | 4/1983 | Japan . |

OTHER PUBLICATIONS

Abstract of Japanese Basic Application 2–060597 (week 9015, 1 Mar. 1990).

Derwent Publications Ltd., Class A11 AN 85–125213, & JP 60 062 996 Kohjin KK, Apr. 11, 1985.

Derwent Publications Ltd., Class D16, AN 90–111092, & JP A 2 060 597 Mitsubishi Acetate, Mar. 1, 1990.

*Primary Examiner*—Ronald W. Griffin
*Attorney, Agent, or Firm*—McAulay Fisher Nissen Goldberg & Kiel

[57] ABSTRACT

A method for reducing the number of contaminative live bacteria in xanthan gum which comprises the step of washing a mixture of 100 parts by weight of water-containing isopropanol having an isopropanol concentration of 50 to 100% by weight and 1 to 100 parts by weight of the xanthan gum under heating conditions.

10 Claims, No Drawings

METHOD FOR REDUCING CONTAMINATIVE LIVE BACTERIA IN XANTHAN GUM

FIELD OF THE INVENTION

The present invention relates to a method for reducing the number of contaminative live bacteria in xanthan gum.

BACKGROUND OF THE INVENTION

Xanthan gum is an anionic polysaccharide produced by the submerged fermentation of a xanthan gum producing bacterium of the genus Xanthomonas. It is used in many industrial fields, including, foods, cosmetics, medicines and the like. In the conventional fermentation processes used for the preparation of xanthan gum, bacteria other than the xanthan-producing bacteria may grow which may survive the process and end up as live bacterial contaminants in the final xanthan product.

In certain of these end uses, and in particular, in food, cosmetic, and medical products, it is preferable that the number of contaminative live bacteria in the xanthan gum decrease as much as possible. Preferably, the number of the bacteria is about 100 or less per gram of the xanthan gum.

In conventional xanthan processing, after the fermentation is completed, an organic solvent in which xanthan is insoluble, typically, isopropanol, is used to precipitate the xanthan from the fermentation broth. Usually the amount of isopropanol used to precipitate the xanthan gum is 1 to 3 times by volume of the volume of the fermentation broth containing the xanthan gum. The precipitated xanthan gum is collected, dehydrated and then directly dried.

In certain procedures for the recovery of xanthan from fermentation broths, the broth may be subjected to a heating step before the precipitation procedure. See, for example, Japanese Provisional Patent Publication 2-60597 which relates to a method for enhancing the efficiency of filtration by sterilizing bacteria by heating after culturing and agglomerating the bacteria.

The xanthan gum producing bacteria are killed by such a heat treatment or by contact with the isopropanol used to precipitate the gum. However, contaminative bacteria can get into the xanthan gum, for example, in a process line, subsequent to the addition of the isopropanol. Contaminative bacteria entering at this point are not killed by the isopropanol present or the heat treatment and end up in the xanthan product as live bacterial contaminant.

Sterilization methods for the reduction of the number of contaminative bacteria in the xanthan gum have been suggested. Such sterilization methods include those described in U.S. Pat. No. 3,206,275 wherein a method for the sterilization of materials, such as, tobacco, spices, rice and the like, by subjecting them to repeated gas treatments, is disclosed. U.S. Pat. No. 3,919,189 discloses a method for sterilization of particulate xanthan gum by intermingling it with gaseous propylene oxide.

However, these methods have some drawbacks in that they do not achieve sufficient sterilization or destruction of the bacterial contaminants. Also, the aqueous xanthan gum solution exhibits decreased transparency and the xanthan gum exhibits decreased solubility (viscosity) in aqueous salt solution. Thus, even in conventional techniques in which a sterilization step is employed, the number of the contaminative live bacteria in xanthan gum camnot be reduced to a satisfactory level.

SUMMARY OF THE INVENTION

It is an object of the present invention to provide a method for reducing the number of contaminative live bacteria in xanthan gum.

It is a further object of the invention to provide a method wherein a sterilization effect sufficient to reduce the contaminative live bacteria can be achieved.

It is another object of the invention to provide a xanthan gum product which exhibits satisfactory reduced levels of live bacterial contaminants to meet the stringent requirements for food, pharmaceutical, and cosmetic end uses.

It is yet another object of the present invention to provide a xanthan gum product which has satisfactory reduced levels of live bacterial contaminants, and which exhibits satisfactory solubility in aqueous salt solution and/or whose aqueous solutions exhibit improved transparency.

We have discovered that the foregoing objects can be achieved contacting a mixture composed of about 1 to 100 parts by weight xanthan gum with 100 parts by of a mixture of water and isopropanol having an isopropanol concentration of 50% to 100% by weight while heating the mixture of xanthan and water/isopropanol at a temperature and for a time period sufficient to reduce the live bacterial contaminants in the resulting xanthan gum to a satisfactory level. Thereafter, the isopropanol is easily removed from the xanthan gum product, e. g., by evaporation, centrifugation, and the like. Accordingly, with the present invention, sterilizing agents which might remain with the xanthan gum product as a residual contaminant are avoided.

In addition, the used isopropanol can be recovered and purified by distillation, which is advantageous from the viewpoint of cost.

DETAILED DESCRIPTION OF PREFERRED EMBODIMENTS

The present invention preferably comprises the steps of suspending xanthan gum recovered from a fermentation broth and which contains contaminative live bacteria in an isopropanol-water mixture solution, and then heating the suspension for a time period and for a temperature sufficient to decrease the contaminative live bacterial content to the desired level. Generally, it is preferable that the contaminative live bacterial content be reduced to a level of no more than about 100 per gram of xanthan gum.

The concentration of isopropanol in the isopropanol-water mixture is in the range of 50% to 100% by weight, preferably 60% to 95% by weight. When the concentration of isopropanol is less than 50% by weight, portions of the xanthan gum may dissolve into a gel state, which interferes with the processing and decreases the sterilization effect.

The amount of the xanthan gum is preferably in the range of 1 to 100 parts by weight per 100 parts by weight of the water-containing isopropanol mixture. If the amount of the xanthan gum is less than about 1 part by weight, the productivity decreases undesirably. If it is more than 100 parts by weight, it is difficult to uniformly suspend the xanthan gum in the mixture and a sufficient sterilization effect cannot be obtained.

The particle diameter of xanthan gum powder to be treated is preferably about 100 microns or less. If the particle diameter of the xanthan gum powder is more than about 100 microns, the sterilization effect is insufficient. The particle diameter of xanthan gum powder to be treated is preferably such that at lest 90% possess a mesh of 105 µm.

The sterilization procedure may be carried out by supplying the particles to the solvent in relatively small portions while stirring to assure a good dispersion of the powder and produce intimate contact of the particles with the solvent. The temperature and the time period may be varied depending on the final results desired. We have found that the heating conditions are preferably in the range of from about 50° to 80° C. If the temperature is less than about 50° C., on occasion, the sterilization effect may be insufficient. If it is more than about 80° C., the physical properties of the aqueous xanthan gum solution deteriorate undesirably. For example, the transparency of a 1% aqueous solution may decrease to less than the desired level of at least 80%, and the viscosity of a 0.5% solution, which desirably is at least out 800 cP can decrease to 300 to 400 cP.

We have found that a heating time of at least about 1 hour or more is sufficient to achieve the desired level of sterilization. However, a heating time of 5 hours or more does not produce further significant sterilization effects and can decrease the productivity.

The heat treatment may be carried out under at a pressure in the range from atmospheric pressure to a slightly a increased pressure of up to about 0.15 MPa. However, no particular restriction is put on the pressure. Normally, the suspension is stirred to give a uniform mixture during the treatment.

After the heat treatment, the mixture of the xanthan gum and isopropanol is dehydrated in a conventional manner, such as, filtration or centrifugal separation, and then dried.

The following Examples illustrate the invention:

EXAMPLES 1 TO 7, AND COMPARATIVE EXAMPLES 1 TO 4

Xanthan gum was produced as follows:

A preculture medium of *Xanthomonas campestris* was prepared using a conventional procedure by culturing the bacteria for 24 hours. The strain used for this purpose was ATCC 13951, however, any conventional xanthan-producing strain may be used.

A 1.8 liter sample of this preculture was inoculated into a 30 liter fermenter containing a culture medium having the following composition:

| Glucose | 58 g/l |
|---|---|
| Polypeptone | 2 g/l |
| $KH_2PO_4$ | 2 g/l |
| $MgSO_4.7H_2O$ | 0.5 g/l |
| Water | 16.2 l |

The bacteria were subjected to submerged fermentation with stirring under aeration at a pH of 6.5 to 7.0 for 2 days to obtain a fermentation broth containing 30 g/l of the xanthan gum. The thus obtained fermentation broth was mixed with 1 to 1.5 times by weight of isopropanol, and the xanthan gum was collected and dried.

The dried xanthan gum was milled to produce three samples with 40%, 75% and 90% permeability through a 105 μm mesh as shown in Table 1; contained a live bacterial number as determined by the most probable number method as described hereinafter of 2400 bacteria/gram. The samples were subjected to sterilization under the conditions shown in Examples 1 to 7 and Comparative Examples 1 to 4 in Table 1. The sterilization procedure used for these examples was described above. During the sterilization, the mixture was stirred at from about 1000 to 1400 rpm at atmospheric pressure. The xanthan gum was separated by centrifugation at 5000 rpm for 10 minutes and then dried at 60° C. The results are shown in Tables 1 and 2.

Each sterilization was carried out in a 5 liter vertical stirring reactor. With regard to the physical properties of the products, the light transmittance in a 1% aqueous solution (wavelength=2 cm cell, transmitted light=650 nm) and viscosity in a 12% aqueous NaCl solution (the xanthan gum= 0.5%) were measured, and a comparison was made between the values obtained before and after the sterilization. The light transmittance measurements were carried out using a Kotaki 5E type photo colorimeter. Viscosity was measured using a BL type Rotor No. 3 provided by Tokimek. Each sample was measured once at 20° C.

The number of contaminative live bacteria was measured in accordance with a most probable number method. Conditions and results are shown in Tables 1 and 2. The above-mentioned most probable number method is carried out as follows:

27 g of sterile water is added to 3 g sample of xanthan gum to prepare a 10% aqueous solution of the sample. This sample solution is referred to as the stock solution. 9 g of sterile water were added to 1 g of this stock solution, and the mixture was then diluted 10 times to obtain a 10 times-diluted stock solution. This 10 times-diluted solution was further diluted 10 times to obtain a 100 times-diluted solution. Afterward, 1 g of each of the thus obtained stock solution, 10 times diluted solution and 100 times-diluted solution was added to each of 3 test tubes, each of which contains 9 g of a culture medium (this makes three groups, each group containing three test tubes, for a total of nine test tubes). The composition of the culture medium was a follows:

| Polypeptone (casein manufacture) | 17 g/l |
|---|---|
| Polypeptone (soybean manufacture) | 3 g/l |
| $KH_2PO_4$ | 2.5 g/l |
| Glucose | 2.5 g/l |
| NaCl | 5 g/l |
| Distilled water | 1 L |

After cultivation at 30° C. for 3 days, the concentration of bacteria in each sample was estimated from a most probable number table on the basis of the number of the test tubes in which the bacteria have grown. The growth of bacteria was determined from visual observation with the naked eye of each test tube for turbidity. Those test tubes in which turbidity was observed were considered to contain growing bacteria. The most probable number procedure used is as described in the USPXXII, Microbiological Tests/Microbial Limit Tests pages 1479–1483.

Comparative examples were carried out using propylene oxide as a sterilizing agent. The procedure used in these examples was to introduce the xanthan gum powder to a vessel and deaerate the vessel. Thereafter, the propylene oxide is introduced, the vessel is sealed and the contents heated to the desired temperature and held at that temperature for the time period indicated. Thereafter, the interior of the vessel is returned to atmospheric pressure by introducing nitrogen and the xanthan recovered. It is noted that as the size of the vessel was one half that for the isopropanol, the amount of xanthan gum treated was also halved. Also an autoclave vessel was used since a vacuum is created in the interior of the vessel during the procedure.

TABLE 1

| | before Sterilization Treatment (inclusive of Treatment Conditions) | | | | | | | |
|---|---|---|---|---|---|---|---|---|
| | Analysis at Initial Stage | | | | | | | |
| | Permeability (% through 105 μm mesh) | Viscosity (cp) | Light Transmittance (%) | Number of Live Bacteria (bacteria/g) | Water-containing Isopropanol (g) (Isopropanol Conc. %) | Xanthan Gum (g) | Time (hr.) | Temperature (°C.) |
| Example 1 | 90 | 1200 | 87.4 | 2400 | 1000 (90%) | 1000 | 1 | 55 |
| Example 2 | 90 | 1200 | 87.4 | 2400 | 1000 (90%) | 1000 | 1 | 75 |
| Example 3 | 90 | 1200 | 87.4 | 2400 | 1000 (90%) | 1000 | 4 | 55 |
| Example 4 | 90 | 1200 | 87.4 | 2400 | 1000 (90%) | 1000 | 4 | 75 |
| Example 5 | 90 | 1200 | 87.4 | 2400 | 1000 (75%) | 1000 | 4 | 75 |
| Example 6 | 90 | 1200 | 87.4 | 2400 | 1000 (60%) | 1000 | 4 | 75 |
| Example 7 | 90 | 1200 | 87.4 | 2400 | 1000 (90%) | 1000 | 4 | 75 |
| Comp. Ex. 1 | 75 | 1200 | 87.4 | 2400 | 1000 (90%) | 1000 | 4 | 75 |
| Comp. Ex. 2 | 40 | 1200 | 87.4 | 2400 | 1000 (90%) | 1000 | 4 | 75 |
| Comp. Ex. 3* | 90 | 1200 | 87.4 | 2400 | 0.5 g (0.1% PO) | 500 | 4 | 50 |
| Comp. Ex. 4* | 90 | 1200 | 87.4 | 2400 | 1.5 g (0.3% PO) | 500 | 4 | 50 |

*As a comparative example, the sterilization treatment was carried out in a 2 liter vertical autoclave
PO: Propylene oxide - % by weight of xanthan gum

TABLE 2

| | Analysis after Treatment | | | |
|---|---|---|---|---|
| | Viscosity (cp) | Light Transmittance (%) | Number of Live Bacteria (bacteria/g) | Reduction of Contaminative Live Bacteria (%) |
| Example 1 | 1180 | 84.4 | 460 | 82 |
| Example 2 | 1200 | 85.2 | <3 | >99 |
| Example 3 | 1190 | 84.8 | 240 | 90 |
| Example 4 | 1220 | 86.0 | <3 | >99 |
| Example 5 | 1160 | 85.0 | 93 | 96 |
| Example 6 | 1200 | 87.0 | 210 | 91 |
| Example 7 | 1210 | 84.0 | 93 | 96 |
| Comp. Ex. 1 | 1170 | 85.0 | 500 | 79 |
| Comp. Ex. 2 | 1190 | 84.0 | 1100 | 54 |
| Comp. Ex. 3* | 400 | 69.5 | 2400 | 0 |
| Comp. Ex. 4* | 280 | 64.4 | 1100 | 54 |

*As a comparative example, the sterilization treatment was carried out in a 2 liter vertical autoclave.

It can be shown from the results of the above-mentioned Examples 1 to 7 and Comparative Examples 1 to 4 that good sterilization effects can be obtained under conditions that each mixture of 100 parts by weight of water-containing isopropanol having an isopropanol concentration of 60–95% by weight and 1 to 100 parts by weight of xanthan gum is heated and held at 50°–80° C. for 1 hour or more, and under conditions that the particle diameter of said xanthan gum is such that at least 90% possess a mesh of 105 μm.

What is claimed is:

1. A method for reducing the number of contaminative live bacterial in xanthan gum which comprises the step of washing a mixture of 100 parts by weight of water-containing isopropanol having an isopropanol concentration to 50% to 100% by weight and 1 to 100 parts by weight of particulate xanthan gum having a particle diameter of about 100 μm or less while heating the mixture at a temperature of from about 50° to about 80° C. for a heating time of at least about one hour.

2. The method according to claim 1 wherein the particle diameter of said xanthan gum is such that at least 90% passes a mesh of 105 μm.

3. The method according to claim 1 or 2 wherein said isopropanol concentration in water-containing isopropanol is in the range of 60% to 95% by weight.

4. The method according to claim 1 or 2 wherein said mixture is contacted at a pressure from atmospheric to about 0.15 MPa.

5. The method according to claim 1 wherein the xanthan gum product has a contaminative bacterial content of no more than 100 per gram of xanthan gum.

6. Xanthan gum product produced by the method of claim 1.

7. Xanthan gum product produced by the method of claim 2.

8. Xanthan gum product produced by the method of claim 3.

9. Xanthan gum product produced by the method of claim 4.

10. Xanthan gum product produced by the method of claim 5.

* * * * *